United States Patent [19]

Noceti et al.

[11] Patent Number: 4,769,504

[45] Date of Patent: Sep. 6, 1988

[54] PROCESS FOR CONVERTING LIGHT ALKANES TO HIGHER HYDROCARBONS

[75] Inventors: Richard P. Noceti; Charles E. Taylor, both of Pittsburgh, Pa.

[73] Assignee: The United States of America as represented by the United States Department of Energy, Washington, D.C.

[21] Appl. No.: 45,634

[22] Filed: Mar. 4, 1987

[51] Int. Cl.$^4$ ............................................... C07C 2/42
[52] U.S. Cl. ................................. 585/415; 585/500; 585/504; 585/657; 585/901; 585/935
[58] Field of Search ............... 585/500, 504, 641, 704, 585/903, 943, 415, 417, 640; 502/225

[56] References Cited

U.S. PATENT DOCUMENTS

| | | |
|---|---|---|
| 2,488,083 | 11/1949 | Gorin et al. |
| 2,575,167 | 11/1951 | Fontana et al. |
| 2,737,414 | 3/1956 | Wenzel |
| 2,739,876 | 3/1956 | Felger |
| 2,752,401 | 6/1956 | Joseph ................................. 570/241 |
| 2,752,402 | 6/1956 | Pye ..................................... 570/241 |
| 3,284,055 | 11/1966 | Johansen |
| 3,322,506 | 5/1967 | Wempe et al. |
| 3,495,949 | 2/1970 | Nieder et al. |
| 3,519,397 | 7/1970 | Bogdanov et al. |
| 3,894,103 | 7/1975 | Chang et al. |
| 3,894,104 | 7/1975 | Chang ............... 585/415 X |
| 3,894,105 | 7/1975 | Chang et al. |
| 3,894,107 | 7/1975 | Butter et al. |
| 3,928,483 | 12/1975 | Chang ................. 585/322 |
| 4,123,380 | 10/1978 | Pieters ..................... 502/225 X |
| 4,123,389 | 10/1978 | Pieters et al. |
| 4,194,990 | 3/1980 | Pieters ..................... 502/225 X |
| 4,339,206 | 7/1982 | Ahs |
| 4,433,192 | 2/1984 | Olah |
| 4,465,893 | 8/1984 | Olah |
| 4,513,092 | 4/1985 | Chu ....................... 502/71 |
| 4,513,164 | 4/1985 | Olah |
| 4,543,434 | 9/1985 | Chang |
| 4,612,088 | 9/1986 | Nardi |

FOREIGN PATENT DOCUMENTS 0117731 2/1984 European Pat. Off. .
55-73619 4/1980 Japan .
84/00429 12/1984 PCT Int'l Appl. .

OTHER PUBLICATIONS

Conner, W. C., Jr. et al., "Oxyhydrochlorination of Methane on Fumed Silica-Based Cu, K, La Catalyst: III, Bulk & Surface Analysis", Applied Catalysis, vol. 11, pp. 59-71, (1984).
Conner, W. C., Jr. et al., "Oxyhydrochlorination of Methane on Fumed Silica-Based Cu, K, La Catalysts: II, Gas Phase Stoichiometry", Applied Catalysis, vol. 11, pp. 49-58, (1984).
PCT International Publication No. WO85/02608, Jun. 20, 1985.
Pieters et al., "The Oxyhydrochlorination of Methane On Fumed Silica-Based Cu$^{+1}$, K, La Catalysts: Parts, I, II, and III, Applied Catalysts, 11 (1984), pp. 35-71.
Noceti and Taylor, "A Process for Conversion of Methane to Higher Hydrocarbons: Presentation at the 25th Spring Symposium of the Pittsburgh-Cleveland Catalysis Society, Cleveland, Ohio, May 15, 1986.

Primary Examiner—William R. Dixon, Jr.
Assistant Examiner—James M. Hunter, Jr.
Attorney, Agent, or Firm—Hugh W. Glenn; Robert J. Fisher; Judson R. Hightower

[57] ABSTRACT

A process is disclosed for the production of aromatic-rich, gasoline boiling range hydrocarbons from the lower alkanes, particularly from methane. The process is carried out in two stages. In the first, alkane is reacted with oxygen and hydrogen chloride over an oxyhydrochlorination catalyst such as copper chloride with minor proportions of potassium chloride and rare earth chloride. This produces an intermediate gaseous mixture containing water and chlorinated alkanes. The chlorinated alkanes are contacted with a crystalline aluminosilicate catalyst in the hydrogen or metal promoted form to produce gasoline range hydrocarbons with a high proportion of aromatics and a small percentage of light hydrocarbons ($C_2$–$C_4$). The light hydrocarbons can be recycled for further processing over the oxyhydrochlorination catalyst.

17 Claims, 3 Drawing Sheets

PROCESS FOR CONVERTING LIGHT ALKANES TO HIGHER HYDROCARBONS

CONTRACTUAL ORIGIN OF THE INVENTION

The United States Government has rights in this invention pursuant to the Employer/Employee agreement of the inventors with the U.S. Department of Energy.

BACKGROUND OF THE INVENTION

This invention relates to the production of higher hydrocarbons from the lower alkanes. It is particularly applicable to the production of gasoline boiling range hydrocarbons from methane.

The need to supplement petroleum supplies has stimulated research and the production of chemicals and fuels from other sources. Methane from natural gas and from the conversion of coal is a source of considerable interest for such production.

It is well known that methane can be converted to methanol by reformation with steam and the methanol thus produced further processed over a crystalline aluminosilicate catalyst to form gasoline boiling range hydrocarbons. Such a process is described in U.S. Pat. No. 3,928,483 to Chang et al.

It is also recognized in PCT International Publication No. WO85/02608 that higher hydrocarbons can be prepared from substituted alkanes, particularly monohalomethanes, by reaction over crystalline aluminosilicate zeolite catalysts. Unfortunately, a continued problem with these processes is the destruction of the zeolite catalysts where water or HCl are present. It was believed that HCl de-aluminates crystalline aluminosilicates leading to their framework collapse and lost catalytic activity.

Monohalomethanes can be prepared as disclosed in European Patent Application No. 0117731 and as suggested in the above cited PCT Publication, converted to higher hydrocarbons over crystalline aluminosilicates. It has long been thought that the monohalides are much preferred in such processes with only low levels of polyhalogenated alkanes tolerated for effective conversion. Such monohalomethanes can be produced by reaction of chlorine or other halogens with methane which requires elevated temperatures above 450° C. or by the oxyhalogenation of methane using a suitable catalyst such as the halide salts of copper, nickel, iron or palladium. Such procedures as are described in the above cited European Patent Application are characterized by low conversions, generally less than about 35%.

An oxyhydrochlorination catalyst containing copper chloride, potassium chloride and a rare earth chloride is disclosed in U.S. Pat. No. 4,123,389 to Pieters et al. This catalyst is reported to provide substantially higher values of methane conversion, but to result in substantial polychlorination. Previously this catalyst was of particular interest in the production of carbon tetrachloride as a feedstock for polychloro-refrigerants.

U.S. Pat. No. 4,513,092 to Chu et al. describes an attempt to combine catalysts for the halogenation-condensation of alkanes. In this patent, a dual-function catalyst including cupric halide, an alkaline earth halide or alkali metal halide and a rare earth halide on a crystalline aluminosilicate catalyst is disclosed. The catalyst is used to promote the conversion of methane to higher hydrocarbons in a single reactor. It is noted that methane conversions of less than 10 mole percent are reported. It is also noted in this reference that deleterious effects may result unless halogen acid gas concentrations are limited especially where such gases could combine with water.

SUMMARY OF THE INVENTION

In view of the above, it is an object of the present invention to provide a process for the conversion of lower alkanes to higher hydrocarbons with improved conversion efficiency.

It is a further object to provide a conversion process in which lower alkanes are converted to an aromatic rich gasoline boiling range fraction.

It is also an object to provide a conversion process employing crystalline aluminosilicate zeolites as catalysts with minimal degradation and de-aluminization.

It is a further object of the invention to provide a two-stage conversion process of methane to gasoline boiling range hydrocarbons with recycle of light hydrocarbons to the first stage.

In accordance with the present invention, a process for converting a lower alkane to higher hydrocarbons includes the steps of passing a reaction mixture containing the lower alkanes along with HCl and $O_2$ in the presence of an oxyhydrochlorination catalyst to form an intermediate gaseous mixture including a chlorinated alkane and water. The intermediate gaseous mixture is dried to less than about $-40°$ C. dew point and passed into contact with a crystalline aluminosilicate catalyst at a temperature in excess of 200° C. to form a product mixture containing dry HCl and higher hydrocarbons than the lower alkane. The dry HCl is separated from the product mixture and recycled into contact with the oxyhydrochlorination catalyst for reaction with the lower alkane and oxygen.

In further aspects of the invention, the lower alkane is methane and the oxyhydrochlorination catalysts includes copper chloride, alkali metal chloride and a rare earth chloride on a refractory oxide support selected from silica, alumina or titania.

In other aspects of the invention, the crystalline aluminosilicate catalyst includes a zeolite such as HZSM-5 or FE-ZSM-5.

In other aspects of the invention, the intermediate gas mixture includes a mixture of methyl chloride, methylene chloride and chloroform.

In one other aspect of the invention, the hydrocarbon product includes C3 to C10 hydrocarbons including in excess of 10 mole percent aromatic hydrocarbons.

In another aspect, the light hydrocarbons including C2–C4 constituents are separated from the hydrocarbon product and recycled to the oxyhydrochlorination stage.

DETAILED DESCRIPTION OF THE DRAWINGS

The present invention is illustrated in the accompanying drawings wherein.

DETAILED DESCRIPTION OF THE INVENTION

Figure 1:
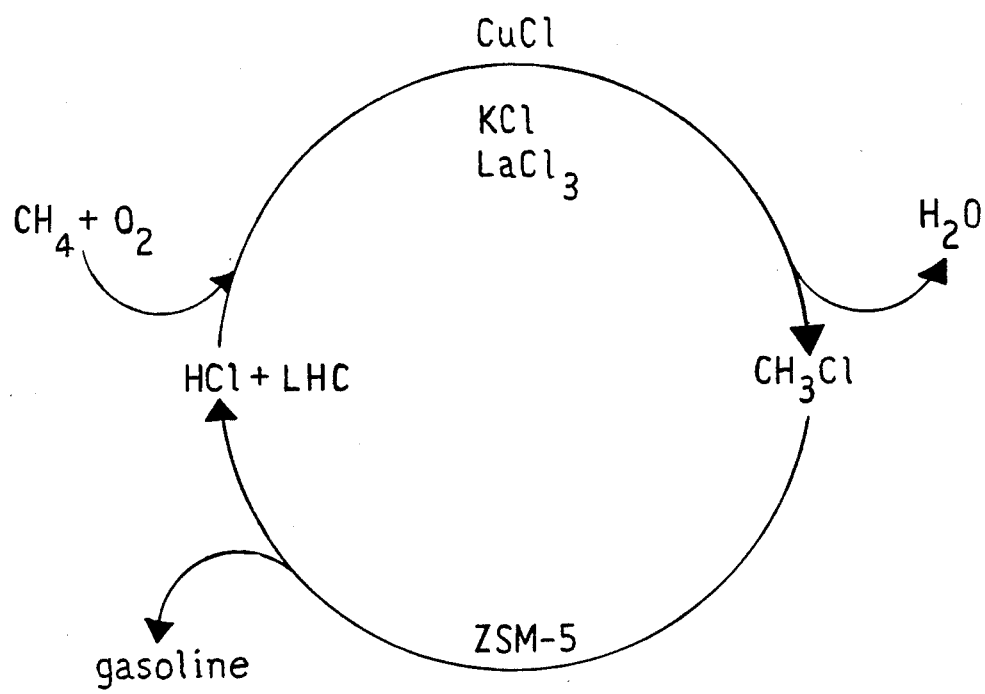
FIG. 1 is a diagrammatic representation of a process cycle.

One manner of performing the process of the present invention is illustrated diagrammatically in FIG. 1. A gaseous feed stream of methane and oxygen along with recycled HCl and light hydrocarbons are reacted over an oxyhydrochlorination catalyst. Although, halides of a large number of metals, such as copper, nickel, iron, lead and cobalt supported on refractory oxides such as silica, alumina or titania are contemplated as the oxyhydrochlorination catalyst, it is preferred that a catalyst of copper chloride, alkali metal chloride and rare earth chloride be employed. In particular, a catalyst of copper chloride, potassium chloride and lanthanum trichloride supported on anhydrous, pyrogenic silica is preferred.

Although the feed into the oxyhydrochlorination reaction can be provided in stoichiometric proportion of about 2:2:1 for $CH_4:HCl:O_2$ respectively, there are certain advantages for the use of excess methane. The oxyhydrochlorination reaction is exothermic requiring the removal of heat from the reactor. Heat transfer and reactor temperature control are greatly improved by the presence of a diluent gas flow in the reaction chamber. Conveniently, nitrogen diluent can be provided if air or oxygen enriched air is selected as a source of oxygen reactant. As will be discussed below, the removal of nitrogen introduced with air can involve additional processing steps and a more complex process. The substitution of excess methane for nitrogen diluent conveniently permits recycle to the oxyhydrochlorination reaction while providing good reactor control and heat transfer conditions. In this regard, the heat capacity at constant pressure and 350° C. of methane is about twice that of nitrogen. Furthermore, excess methane of up to 500% of that stoichiometrically required can provide an improvement in HCl conversion.

It will be understood that the feed to the oxyhydrochlorination reaction can be provided from various sources including natural gas, producer gas, air, oxygen and various sources of HCl mixed in the desired proportion to obtain the feed mixture.

As illustrated in FIG. 1, methyl chloride and water are principle reaction products of the oxyhydrochlorination reaction. The inventors have found that the removal of water and drying of this intermediate reaction gas product is of utmost importance in the efficient operation of this process. As will be discussed below, the catalyst activity and the conversion of light haloalkanes to higher hydrocarbons can be severely impaired by certain reaction products. Although, prior processes, such as those for the production of higher hydrocarbons from methanol have operated with zeolite catalysts in the presence of water, it is of considerable advantage in the present process to remove water following the first reaction stage.

The water can be removed from the intermediate reaction gases in two stages. For example, a water-cooled condenser followed by a molecular sieve or alumina absorbent can be employed. It is of importance that the gas be dried to a dew point of at least −40° C. and preferably to −60°−−80° C. to insure against formation of HCl-water mixtures in the chloroalkane condensation reaction.

Although the major product from the oxyhydrochlorination reaction is expected to be methyl chloride, it is of advantage to also have higher halogenated hydrocarbons such as chloroform or methylene chloride present. These more highly substituted chloroalkanes can also be condensed over the zeolite catalysts to higher boiling hydrocarbons and may add to the proportions of aromatic and branch chain aliphatic hydrocarbons in the product.

In the second stage, the halogenated hydrocarbons are allowed to contact a crystalline aluminosilicate zeolite in either the hydrogen promoted or the iron promoted form. Particularly preferred zeolites are HZSM-5 or FE-ZSM-5. The reaction products of the zeolite catalysts depend on the residence time, pressure and temperature of the reaction gases. Residence times of 0.1 to 10 seconds, pressures of 1–20 atmospheres and temperatures of 200°–550° C. are contemplated. The reaction product is a mixture of aliphatic and aromatic hydrocarbons in the gasoline boiling range along with lighter hydrocarbons and hydrogen chloride. As will be described, the light hydrocarbons and the HCl are separated from the product stream and recycled into the first stage of the process for oxyhydrochlorination.

It is an important and significant aspect of the invention that the process can be operated so that a fraction of the second stage product including light hydrocarbons and unreacted reactants from the original feed stock may be recycled into the oxyhydrochlorination stage. This flexibility allows easy shifting of product distribution towards higher molecular weight and greater proportions of aromatic compounds. In addition, excess methane feed is conveniently employed and returned to the first reaction stage.

Figure 2:
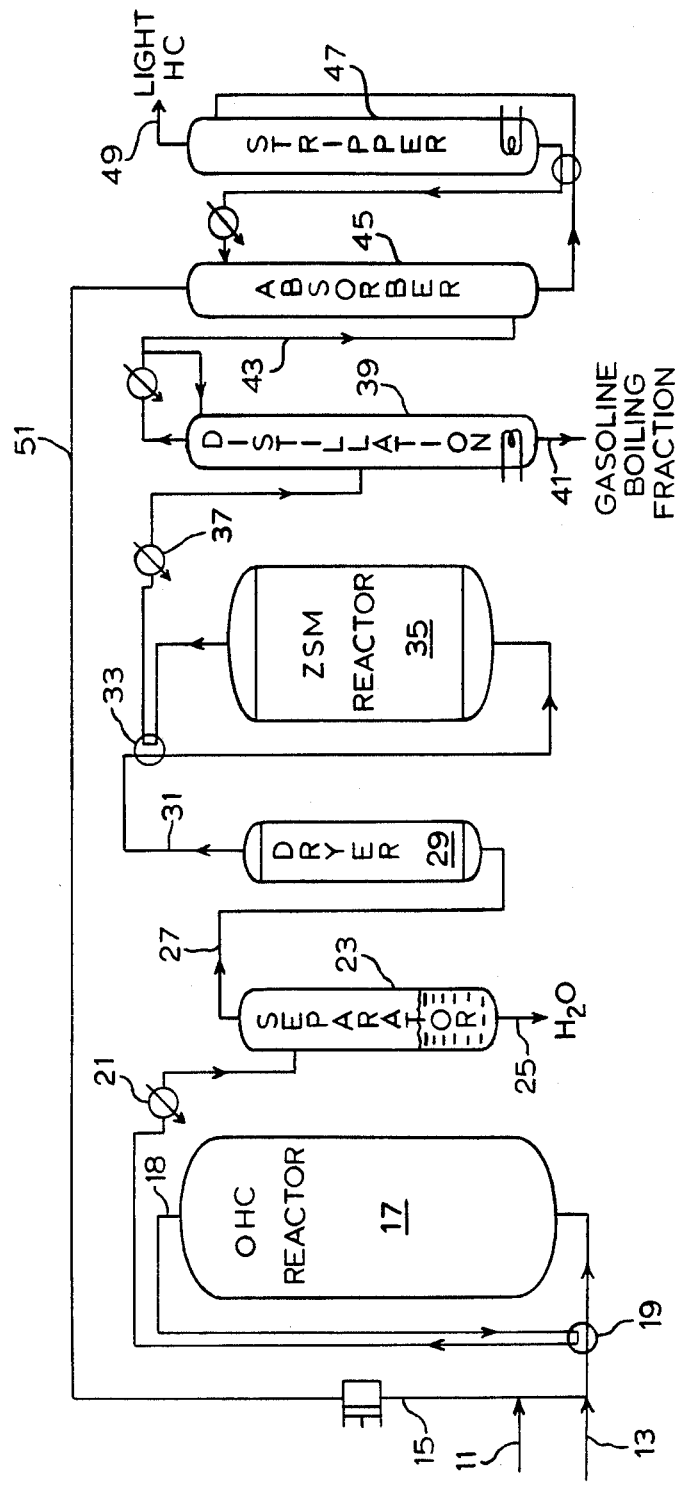
FIG. 2 is a flow diagram of a process for converting a lower alkane to higher hydrocarbons.

Referring now to FIG. 2, a more detailed description of one embodiment of the present invention is given. Methane 11 along with oxygen 13 and recycle gases including HCl 15 are preheated and introduced into the oxyhydrochlorination reactor illustrated at 17. Typically, the reaction is carried out at a temperature of 200°–350° C. and a pressure of 10–20 atmospheres over a catalyst of, for instance $CuCl-KCl-LaCl_3$ supported on anhydrous, pyrogenic silica. The intermediate gaseous products 18 are cooled to preheat the oxygen feed in preheater 19 followed by condenser 21 to begin water removal at 30° C. to 40° C. Water, possibly with small amounts of methylene chloride, chloroform and unreacted HCl, is collected in separator 23 and withdrawn from the process at 25. Where required for economy, these chlorinated materials can be recovered by fractionation and returned to the process. The intermediate gaseous mixture 27 is further dried over a molecular sieve or an alumina desiccant in Dryer 29 to obtain a dew point of at least −40° C., preferably −60° to −80° C. Drying is enhanced by pressures in the range of 10 to 20 atmospheres.

The dried reactant gases at 31 including methyl chloride, methylene chloride and in some instances chloroform are preheated at 33 and passed into the second reactor 35 for contact with a crystalline aluminosilicate catalyst. Preferably, a shape selective catalyst in the hydrogen or iron promoted form of ZSM-5 is employed. The reaction product gases are further processed by cooling and condensing at about 30° C. to 40° C. at 37 for feed into fractionating column 39 from which a gasoline boiling fraction 41 is obtained.

The gasoline boiling fraction 41 typically includes hydrocarbons from the C5 to C10 range with an average molecular weight of about 90 to 100, boiling at temperatures of about 30° to 200° C. The present process advantageously produces a high proportion of aromatics and branched hydrocarbons that are of considerable value as gasoline blending stocks.

The column overhead 43 passes to an absorber stripper combination at 45 and 47 for separating the light hydrocarbons 49 from the HCl excess methane and any inert gases at 51. Light hydrocarbons 49 can include C3–C5 hydrocarbons and possibly some ethane. This light fraction can be withdrawn for other use or advantageously recycled with the HCl and unreacted methane at 51 to the oxyhydrochlorination reactor 17. The recycle of the light hydrocarbons will greatly increase the yield of the gasoline boiling range fraction at 41 and it is one of the advantageous aspects of the present invention.

Figure 3:
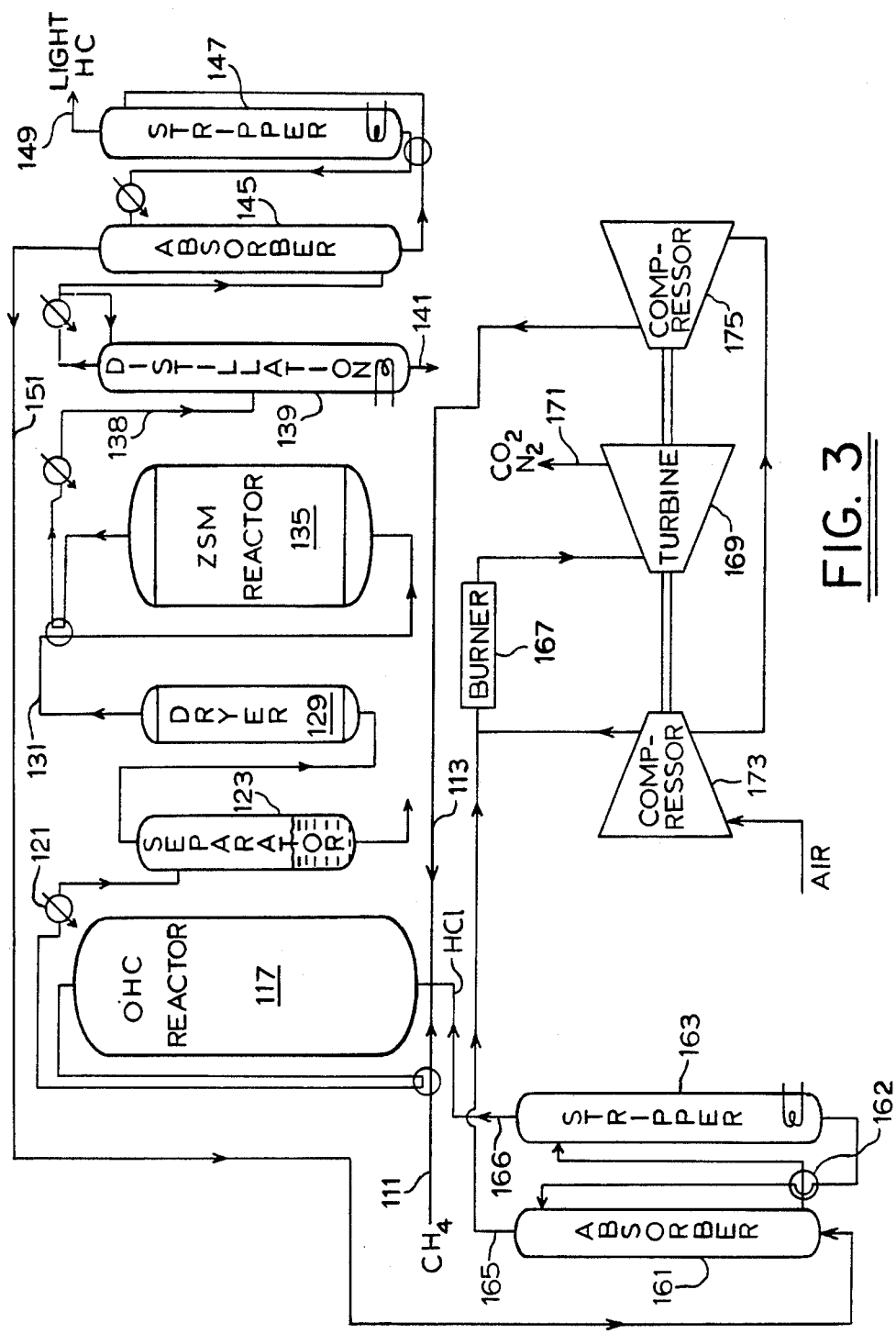
FIG. 3 is a flow diagram of an alternate embodiment of a process for converting a lower alkane to higher hydrocarbons.

The embodiment illustrated in FIG. 3 shows how air can be employed to supply oxygen to the oxyhydrochlorination reaction. As in the FIG. 1 and FIG. 2 embodiments, methane, air and HCl are reacted over the oxychlorination catalyst in reactor 117 and water is removed in condenser 121, separator 123 followed by dryer 129. The chlorinated alkanes 131 are condensed to higher hydrocarbons in reactor 135 with zeolite catalysts and the reaction products 138 separated in fractionating column 139 to provide a gasoline boiling range fraction 141, light hydrocarbons 149 and the recycle stream 151. The absorber 145 and the stripper 147 operate in much the same fashion as in the FIG. 2 embodiment.

In the embodiment of FIG. 3, the recycle stream 151 will not only include methane and HCl but also will include the nitrogen introduced in the air stream. The recycle stream can be processed in another absorber 161 and stripper 163 in combination to separate the methane and nitrogen at 165 from the HCl at 166. The HCl at 166 is returned to the oxyhydrochlorination reactor 117 in mixture with methane 111 and air 113.

In order to avoid introduction of water into the system, an organic, weak base solvent is circulated in absorber 161, heat exchanger 162 and stripper 163 to separate the HCl from the methane and nitrogen streams. An absorbent such as a liquid diglyme, for instance, the dimethyl ether of ethylene glycol can be selected for use.

Since it is difficult to separate the methane and nitrogen streams, they are passed to a combustor or burner 167 for providing hot gases, for instance, to drive turbine 169. Nitrogen gas and combustion products can be removed at discharge 171. The work produced by turbine 169 can be used for any purpose but as illustrated, it can be used to drive compressors 173 and 175 for providing air into the process.

The following examples are presently solely by way of illustration of the present invention.

EXAMPLE I

An oxyhydrochlorination catalyst of 41.6% CuCl, 11.5% KCl, 9.4% $LaCl_3$ and 37.5% HS-5 grade CAB-O-SIL (a registered trademark of the Cabot Corp.) was supported within a reaction chamber. A feed of 40% methane, 40% HCl, 18% $O_2$ and 2% $N_2$ was premixed and heated to 172° C. before entering the reaction chamber maintained at 345° C. by means of an external furnace. The gaseous feed contacted the catalyst for about 4 seconds and the products collected in a cold trap employing dry ice and isopropanol solution. The intermediate reaction products were predominantly methyl chloride and water. The water was removed and the methyl chloride dried and passed into a second stage reaction chamber including HZSM-5 maintained at a temperature of 350° C. for 3 seconds. The products were found to be hydrogen chloride, both branched and straight-chain alkanes and aromatic hydrocarbons in the gasoline boiling range.

EXAMPLE II

The second stage reaction chamber was provided with iron promoted ZSM-5, alumino-silicate zeolite catalysts. The reaction was maintained at 350° C. for 5.6 seconds residence time with essentially the same reaction products obtained as in Example I.

EXAMPLE III

The oxyhydrochlorination reaction stage was operated in a manner to obtain a mixture of methyl chloride and methylene chloride as the intermediate reaction products. The second stage reactor with zeolite aluminosilicate catalysts was maintained at 350° C. with a retention time of 4 seconds. An increased aromatics fraction was found over the EXAMPLES I and II products.

EXAMPLE IV

The intermediate reaction products include methyl chloride, methylene chloride and chloroform in molar proportions of about 75 to 22 to 3 respectively. Following a drying step, these materials were condensed to gasoline boiling range alkanes and other light hydrocarbons after reaction over a zeolite catalyst at 350° C. for about 5 seconds.

A number of other runs were made to show the relationship of residence time, conversion and selectivity of product from the oxyhydrochlorination reaction. A feed gas stream of 25–38% $CH_4$, 12.5–19% $O_2$, 5–37.5% $N_2$ and 25–38% HCl was used. The results are given below in Table I.

TABLE I

| Residence[a] Time (SEC) | % Conversion[b] | | | % Product | | | | | |
|---|---|---|---|---|---|---|---|---|---|
| | $CH_4$ | HCl | $O_2$ | $CH_3Cl$ | $CH_2Cl_2$ | $CHCl_3$ | $CCl_4$ | $CO_2$ | HCOOH |
| 4.2 | 25.2 | 30.1 | 34.0 | 75.3 | 19.7 | 1.6 | 0.00 | 0.8 | 2.6 |
| 5.1 | 28.4 | 39.3 | 38.9 | 74.0 | 21.2 | 2.0 | 0.00 | 0.9 | 1.9 |
| 6.1 | 38.4 | 50.7 | 55.2 | 68.4 | 25.8 | 2.9 | 0.01 | 1.4 | 1.4 |
| 6.3 | 36.3 | 57.7 | 58.0 | 67.9 | 26.2 | 2.7 | 0.00 | 1.6 | 1.6 |
| 6.4 | 45.2 | 62.4 | 62.9 | 66.7 | 27.2 | 3.3 | 0.01 | 1.6 | 1.2 |
| 7.1 | 42.1 | 96.4 | 97.4 | 64.9 | 27.5 | 3.8 | 0.01 | 2.2 | 1.6 |
| 9.1 | 53.5 | 98.0 | 92.9 | 57.3 | 32.3 | 6.0 | 0.02 | 3.4 | 0.9 |
| 9.6 | 62.3 | 75.8 | 87.9 | 57.0 | 33.5 | 5.2 | 0.02 | 3.3 | 1.0 |

[a]Residence Time = (catalyst void space)/(total inlet gas flow rate).
[b]% Conversion = 100 ([IN] − [OUT])/[IN].

EXAMPLE V

The oxyhydrochlorination reactor was operated with an excess of methane in a $CH_4:HCl:O_2$ ratio of 10:2:1. HCl conversion was increased from 81% to 90% compared with a stoichiometric reactant ratio of $CH_4:HCl:O_2$ of 2:2:1.

EXAMPLE VI

The oxyhydrochlorination reactor was operated with an excess of methane and a slight excess of oxygen in a $CH_4:HCl:O_2$ ratio of 10:2:1.2. An HCl conversion of 96% and a $CH_3Cl:CH_2Cl_2$ ratio of 4.5:1 was obtained.

It was also found that as temperature increased from 250° C. through 360° C. at constant residence time, that the percent of methyl chloride in the product decreased while the percent of methylene chloride, chloroform and carbon dioxide increased.

The conversion of methane to chloromethanes was observed under varying reaction conditions. Data at constant temperature and pressure is listed below in Table II. Carbon monoxide was not detected in the product stream.

TABLE II
CONVERSION OF METHANE OVER AN OXYHYDROCHLORINATION CATALYST

| | | | |
|---|---|---|---|
| Space Velocity, GHSV (STP) | 47 | 94 | 156 |
| Temperature, °C. | 331 | 330 | 331 |
| Pressure, Atm. | 1 | 1 | 1 |
| $CH_4$ Conversion, Mole % | 42.7 | 22.3 | 18.4 |
| Carbon Product Distribution, Mole % | | | |
| $CH_3Cl$ | 59.6 | 74.8 | 85.1 |
| $CH_2Cl_2$ | 27.9 | 22.7 | 10.7 |
| $CHCl_3$ | 4.6 | 1.5 | 0.6 |
| $CCl_4$ | 0.01 | 0.01 | 0.01 |
| HCOOH | 0.8 | 0.3 | 3.1 |
| CO | 0 | 0 | 0 |
| $CO_2$ | 7.1 | 0.8 | 0.6 |

[1]Feed stream consisted of 40% $CH_4$, 40% HCl, and 20% $O_2$.

In addition to the products given in Tables I and II, trace amounts of 2-chloropropane and 2-chlorobutane were found in the methyl chloride condensation products. It is contemplated that these products can be recycled within the system such that on contact with the crystalline aluminosilicate catalyst, they will be converted to aromtic hydrocarbons and hydrogen chloride.

Other products found in the discharge from the zeolite reactor chamber include pentane, butane, benzene, cyclohexane, hexane, toluene, xylene, 1,3,5-trimethylbenzene, 1,2,3- and 1,2,4-trimethylbenzene, tetramethylbenzene, durene and pentamethylbenzene.

It has been found that by using only dry feed material into the zeolite catalyst reaction chamber that extremely long catalyst life is obtained. After each forty to eighty hours of operation, the catalyst is regenerated by reaction with oxygen gas to burn off carbon deposited on the catalyst surface. The inventors have found that ZSM-5 can be employed for over 800 hours of operation with about 14 regeneration cycles and still maintain methyl chloride conversions of over 98%.

It is also been found that the aromatic fractions in the product can be greatly increased by including methylene chloride and chloroform in the feed materials to the zeolite reaction chamber. Table III below shows that one particularly advantageous mixture of about 75% $CH_3Cl$, 22% $CH_2Cl_2$ and about 3% $CHCl_3$ can provide increases in aromatics by factors of 1.77 and 1.33 based on methanol and methylchloride respectively.

TABLE III

| | Relative aromatic fractions | |
|---|---|---|
| Reactant(s) | Based on $CH_3OH$ | Based on $CH_3Cl$ |
| $CH_3OH$ | 1.00 | 0.75 |
| $CH_3Cl$ | 1.33 | 1.00 |
| $CH_3Cl:CH_2Cl_2:CHCl_3::$ 74.4:22.3:3.3 | 1.77 | 1.33 |

It can be seen that the present invention provides a process for improved conversion of methane to higher boiling point hydrocarbons. Good conversion to the gasoline boiling range can be obtained with lighter hydrocarbons easily recycled through the system to produce additional gasoline boiling range hydrocarbons. It is also seen that zeolite catalysts can be employed with extremely long catalyst life without de-aluminization even in the presence of HCl, provided water has been excluded from the reaction chamber using zeolite as catalyst. It is further seen that by employing a mixture of polychlorinated methanes and methyl chloride as the intermediate reaction materials that a high aromatic fraction can be obtained as product.

Although, the present invention is described in terms of the specific embodiments and process parameters, it will be clear to one skilled in the art that various modifications in the procedures and process can be made within the scope of the following claims.

The embodiment of the invention in which an exclusive property or privilege is claimed is defined as follows:

1. A process for converting a lower alkane to higher hydrocarbons in stages comprising;
   passing a reaction mixture including said lower alkane, HCl and $O_2$ into contact with an oxyhydrochlorination catalyst to form an intermediate gaseous mixture included chlorinated alkanes and water;
   drying said intermediate gaseous mixture to less than about −40° C. dew point;
   passing said dried intermediate gaseous mixture into contact with a crystalline aluminosilicate catalyst at a temperature in excess of 200° C. to form a product mixture containing dry HCl and higher hydrocarbons than said alkane;
   separating said dry HCl from said product mixture and recycling said HCl for reaction with said lower alkane and oxygen in the presence said oxyhydrochlorination catalyst.

2. The process of claim 1 wherein said lower alkane is methane.

3. The process of claim 1 wherein said oxyhydrochlorination catalyst comprises copper chloride, alkali metal chloride and rare earth chloride on a refractory oxide support selected from the group consisting of silica, alumina and titania.

4. The process of claim 3 wherein said oxyhydrochlorination catalyst comprises CuCl, KCl and $LaCl_3$ supported on anhydrous, pyrogenic silica.

5. The process of the claim 1 wherein said crystalline aluminosilicate comprises the zeolite, HZSM-5.

6. The process of claim 1 wherein said crystalline aluminosilicate comprises the zeolite Fe-ZSM-5.

7. The process of claim 1 wherein said dried intermediate gaseous mixture comprises a mixture of methyl chloride, methylene chloride and chloroform.

8. The process of claim 7 wherein methyl chloride, methylene chloride and chloroform are in molar proportions of about 75:22:3.

9. The process of claim 7 wherein said hydrocarbon product includes C-2 to C-10 hydrocarbons with substantially more aromatic fraction than that produced with only methyl chloride in said dried gaseous mixture.

10. The method according to claim 9 wherein said hydrocarbon product mixture is fractionated into a light hydrocarbon mixture containing C-2 through C-4 hydrocarbons and a gasoline boiling range mixture of C-5 to C-10 hydrocarbons having an atmospheric boiling range of 30° C.–200° C., said gasoline boiling range mixture including a major fraction of aromatic hydrocarbons and wherein said light hydrocarbons are recycled to said oxyhydrochlorination catalyst for reaction.

11. The process of claim 1 wherein said reaction mixture includes methane and HCl in about equal molar amounts with methane and wherein $O_2$ is included in about ½ the molar quantity of HCl.

12. The process of claim 1 wherein said reaction mixture includes a stoichiometric excess of methane in the proportions of methane:HCl:$O_2$ of about 10:2:1 respectively.

13. The process of claim 12 wherein said reaction mixture includes a stoichiometric excess of methane and of oxygen over HCl in the proportions of methane:HCl:$O_2$ of about 10:2:1.2 respectively.

14. The method according to claim 1 wherein $O_2$ is supplied in mixture with nitrogen and wherein nitrogen so introduced is removed with methane for combustion and discharged from said process.

15. The method according to claim 1 wherein oxygen is provided in combination with nitrogen in air into the oxyhydrochlorination step and wherein HCl is separated from the product mixture following contact with the crystalline aluminosilicate catalyst by scrubbing with a dry organic, weak base solvent.

16. The method according to claim 1 wherein the intermediate gaseous mixture is dried to less than −40° C. dew point by condensation at about 20°–30° C. followed by contact with a solid desiccant selected from the group consisting of alumina and a zeolite molecular sieve.

17. The method according to claim 16 wherein methylene chloride and chloroform are fractionated from said condensed water and recombined with said dried, gaseous intermediate mixture.

* * * * *